(12) United States Patent
Stein

(10) Patent No.: US 8,421,479 B2
(45) Date of Patent: Apr. 16, 2013

(54) PULSED ECHO PROPAGATION DEVICE AND METHOD FOR MEASURING A PARAMETER

(75) Inventor: Marc Stein, Chandler, AZ (US)

(73) Assignee: NaviSense, Plantation, FL (US)

( * ) Notice: Subject to any disclaimer, the term of this patent is extended or adjusted under 35 U.S.C. 154(b) by 364 days.

(21) Appl. No.: 12/748,088

(22) Filed: Mar. 26, 2010

(65) Prior Publication Data

US 2010/0327848 A1 Dec. 30, 2010

Related U.S. Application Data

(60) Provisional application No. 61/221,901, filed on Jun. 30, 2009.

(51) Int. Cl.
*G01R 27/04* (2006.01)
*G01R 27/32* (2006.01)

(52) U.S. Cl.
USPC .................. 324/642; 324/639; 73/861.18

(58) Field of Classification Search .................. None
See application file for complete search history.

(56) References Cited

U.S. PATENT DOCUMENTS

| | | | |
|---|---|---|---|
| 5,470,354 A | 11/1995 | Hershberger et al. | |
| 5,650,571 A * | 7/1997 | Freud et al. | 73/861.06 |
| 5,683,396 A | 11/1997 | Tokish et al. | |
| 5,688,279 A | 11/1997 | McNulty et al. | |
| 5,871,018 A | 2/1999 | Delp et al. | |
| 6,245,109 B1 | 6/2001 | Mendes et al. | |
| 6,517,487 B1 * | 2/2003 | Mazess et al. | 600/449 |
| 6,583,630 B2 | 6/2003 | Mendes et al. | |
| 6,621,278 B2 | 9/2003 | Ariav | |
| 6,701,174 B1 | 3/2004 | Krause et al. | |
| 6,856,141 B2 | 2/2005 | Ariav | |
| 7,195,645 B2 | 3/2007 | Disilvestro et al. | |
| 7,442,196 B2 | 10/2008 | Fisher et al. | |
| 7,578,821 B2 | 8/2009 | Fisher et al. | |
| 2002/0029784 A1 | 3/2002 | Stark et al. | |
| 2005/0020941 A1 | 1/2005 | Tarabichi | |
| 2006/0058798 A1 | 3/2006 | Roman et al. | |
| 2006/0232408 A1 | 10/2006 | Nyez et al. | |
| 2006/0271112 A1 | 11/2006 | Martinson et al. | |
| 2007/0219561 A1 | 9/2007 | Lavalle et al. | |
| 2007/0272747 A1 | 11/2007 | Woods et al. | |
| 2008/0110262 A1 * | 5/2008 | Ariav et al. | 73/598 |

* cited by examiner

*Primary Examiner* — Minh N Tang

(57) ABSTRACT

At least one embodiment is directed to a sensor for measuring a parameter. A signal path of the system comprises an amplifier (612), a sensor element, and an amplifier (620). The sensor element comprises a transducer (4) at a first location of a waveguide (5), and a reflective surface (30) at a second location of the waveguide (5). A parameter such as force or pressure applied to the sensor element can change the length of waveguide (5). A pulsed energy wave is emitted by the transducer (4) into the waveguide (5) at the first location. The transducer (4) is responsive to pulsed energy waves reflected from reflective surface (30) to the second location. The transit time of each pulsed energy wave is measured. The transit time corresponds to the pressure or force applied to the sensor element.

14 Claims, 8 Drawing Sheets

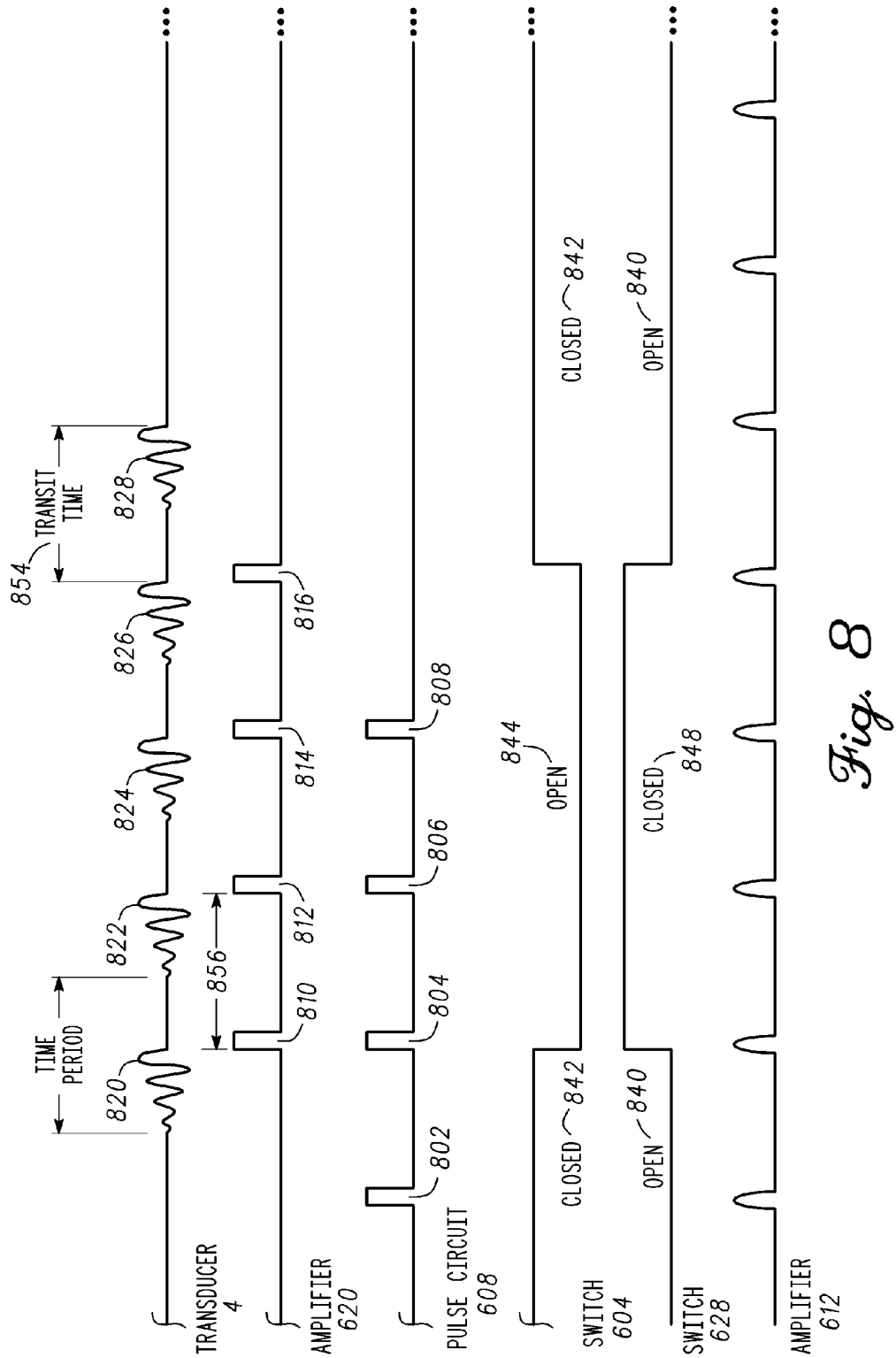

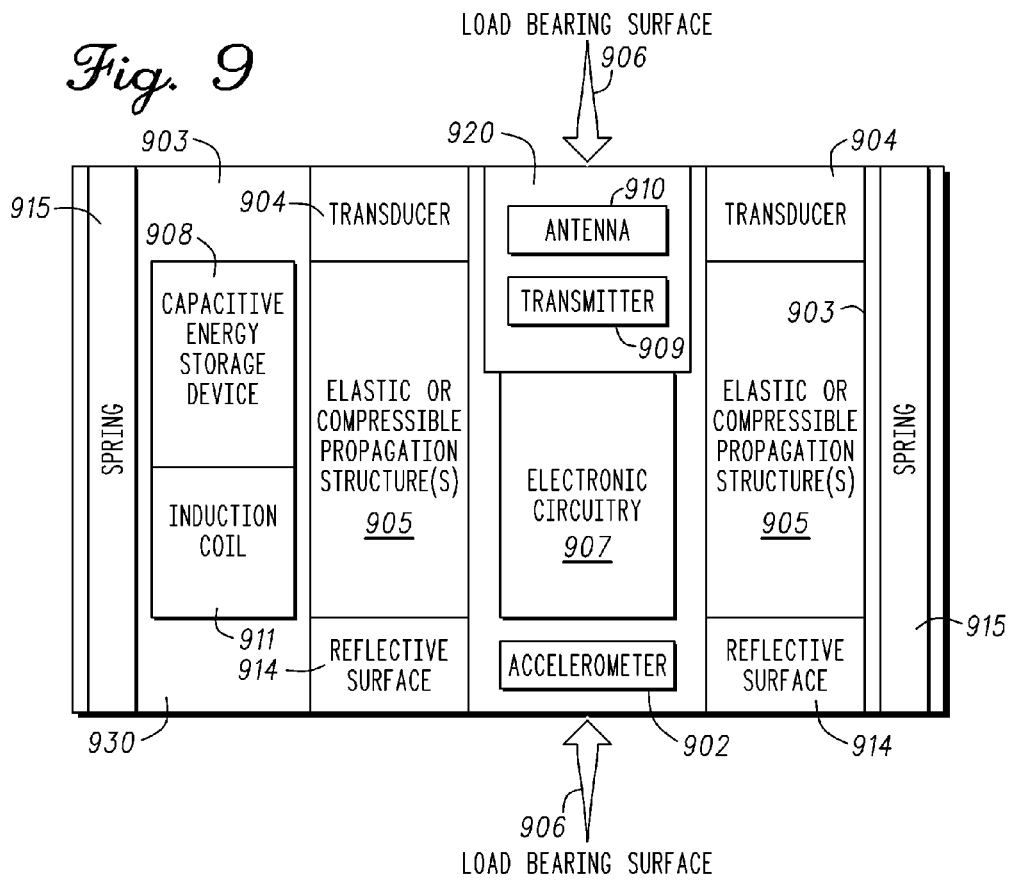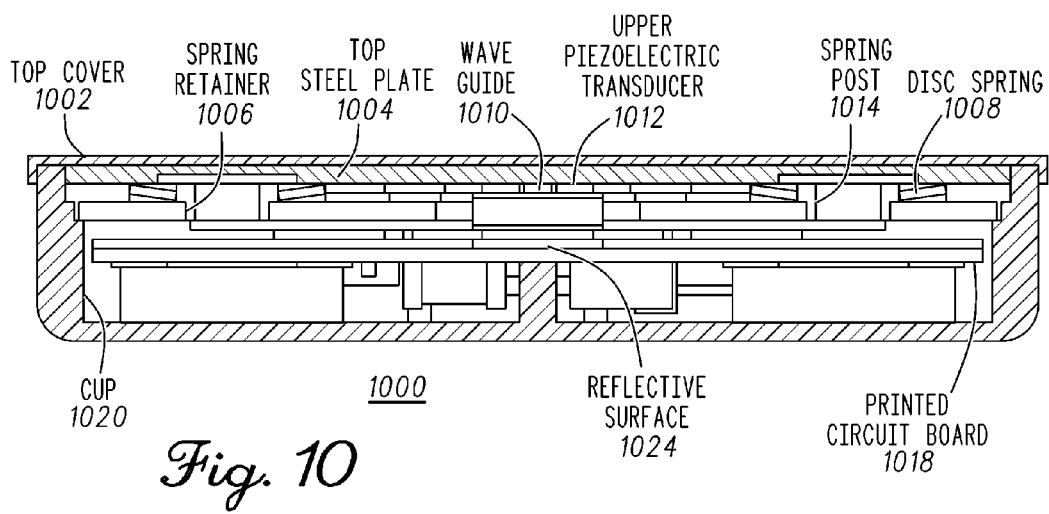

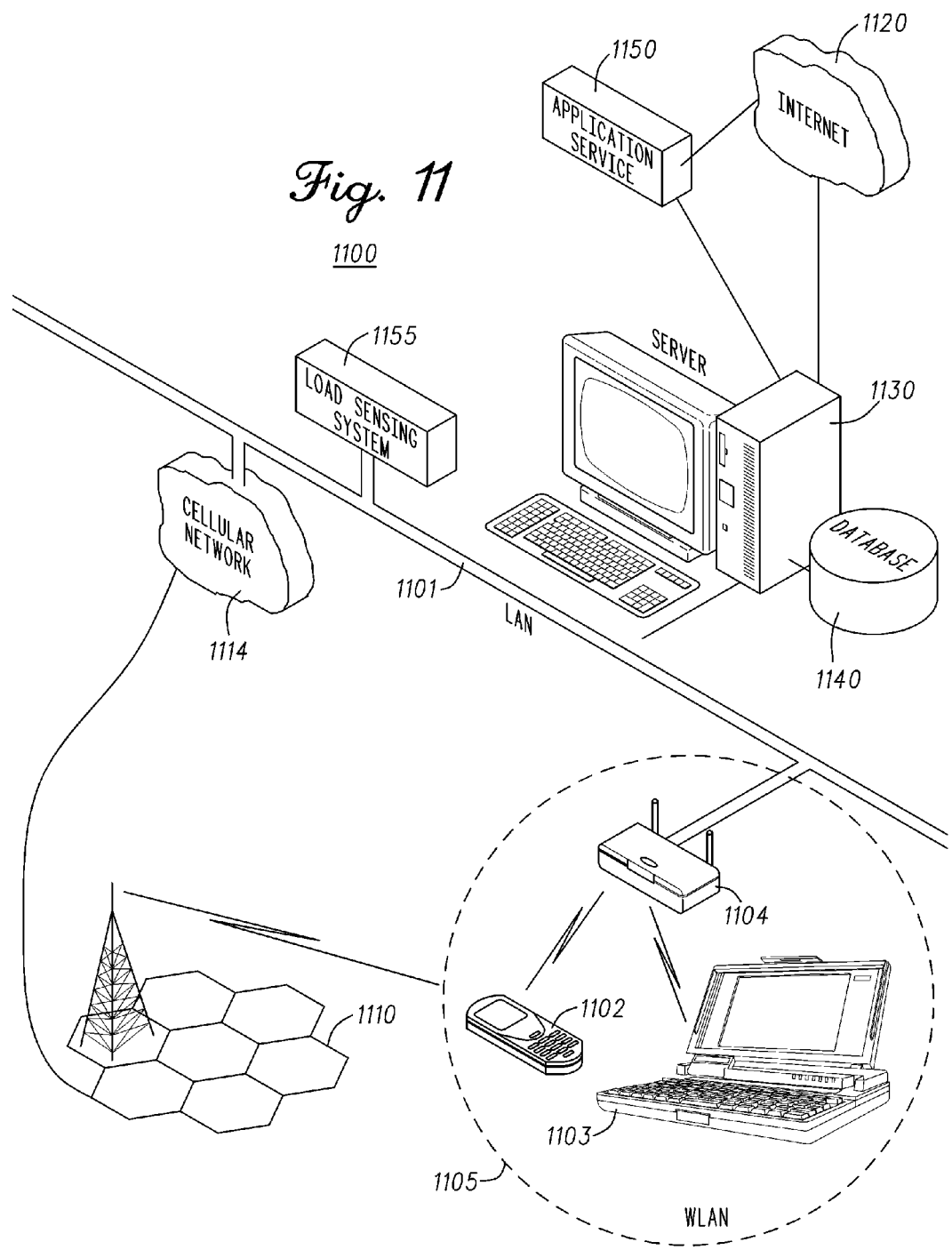

PULSED ECHO PROPAGATION DEVICE AND METHOD FOR MEASURING A PARAMETER

CROSS-REFERENCE TO RELATED APPLICATIONS

This application claims the priority benefit of U.S. provisional patent application Ser. Nos. 61/221,761, 61/221,767, 61/221,779, 61/221,788, 61/221,793, 61/221,801, 61/221,808, 61/221,817, 61/221,867, 61/221,874, 61/221,879, 61/221,881, 61/221,886, 61/221,889, 61/221,894, 61/221,901, 61/221,909, 61/221,916, 61/221,923, and 61/221,929 all filed 30 Jun. 2009. The disclosures of which are incorporated herein by reference in its entirety.

FIELD

The disclosure relates in general to measurement, and particularly though not exclusively, is related to a structure and method to measure a parameter.

BACKGROUND

Sensors are used to provide information to a device or system. The sensor information can be critical to device operation or provide additional data on the system or an external environment. For example, a temperature sensor is commonly used to monitor the operating temperature of components. The temperature sensor can be used to monitor average operating temperatures and instantaneous operating extremes. Sensor data can be used to understand how device functions or performs in different working environments, users, and environmental factors. Sensors can trigger an action such as turning off the system or modifying operation of the system in response to a measured parameter.

In general, cost typically increases with the measurement precision of the sensor. Cost can limit the use of highly accurate sensors in price sensitive applications. Furthermore, there is substantial need for low power sensing that can be used in systems that are battery operated. Ideally, the sensing technology used in low-power applications will not greatly affect battery life. Moreover, a high percentage of battery-operated devices are portable devices comprising a small volume and low weight. Device portability can place further size and weight constraints on the sensor technology used. Thus, form factor, power dissipation, cost, and measurement accuracy are important criteria that are evaluated when selecting a sensor for a specific application.

BRIEF DESCRIPTION OF THE DRAWINGS

Exemplary embodiments of present invention will become more fully understood from the detailed description and the accompanying drawings, wherein:

FIG. 8 is a timing diagram of a measurement system in accordance with an exemplary embodiment;

FIG. 9 is an exemplary block diagram of the components of a sensing module;

FIG. 10 depicts a cross sectional view of a sensing module in further detail according to one embodiment; and FIG. 11 is a communication network for sensing applications in accordance with an exemplary embodiment.

DETAILED DESCRIPTION OF EXEMPLARY EMBODIMENTS

Figure 1:
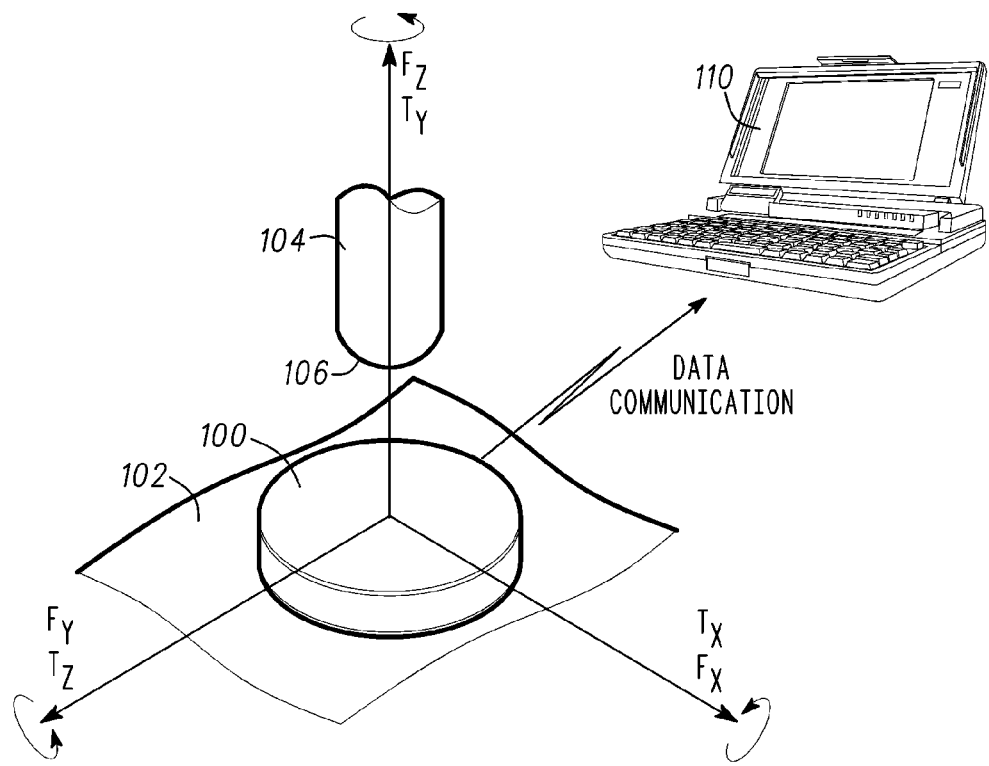
FIG. 1 is an illustration of a sensor module subjected to a parameter in accordance with an exemplary embodiment.

The following description of exemplary embodiment(s) is merely illustrative in nature and is in no way intended to limit the invention, its application, or uses.

Processes, techniques, apparatus, and materials as known by one of ordinary skill in the art may not be discussed in detail but are intended to be part of the enabling description where appropriate. For example specific computer code may not be listed for achieving each of the steps discussed, however one of ordinary skill would be able, without undo experimentation, to write such code given the enabling disclosure herein. Such code is intended to fall within the scope of at least one exemplary embodiment.

Additionally, the sizes of structures used in exemplary embodiments are not limited by any discussion herein (e.g., the sizes of structures can be macro (centimeter, meter, and larger sizes), micro (micrometer), nanometer size and smaller).

Notice that similar reference numerals and letters refer to similar items in the following figures, and thus once an item is defined in one figure, it may not be discussed or further defined in the following figures.

In all of the examples illustrated and discussed herein, any specific values, should be interpreted to be illustrative only and non-limiting. Thus, other examples of the exemplary embodiments could have different values.

FIG. 1 is an illustration of a sensor 100 in accordance with an exemplary embodiment. Sensor 100 is placed in a position where a parameter to be measured can be applied to the device or affects the device indirectly. In a non-limiting example, a force or pressure is used to illustrate measuring a parameter using sensor 100. Sensor 100 is placed between a surface 102 and a surface 106 of object 104. A compressive force is applied to sensor 100. In general, embodiments of sensor 100 are broadly directed to measurement of physical parameters, and more particularly, to evaluating changes in the transit time of a pulsed energy wave propagating through a medium.

In at least one exemplary embodiment, an energy pulse is directed within one or more waveguides in sensor 100 by way of pulse mode operations and pulse shaping. The waveguide is a conduit that directs the energy pulse in a predetermined direction. The energy pulse is typically confined within the waveguide. A transit time of an energy pulse through a medium is related to the material properties of the medium. This relationship is used to generate accurate measurements of parameters such as distance, weight, strain, pressure, wear, vibration, viscosity, and density to name but a few.

Sensor 100 can be size constrained by form factor requirements of fitting within a region of a device or system. In a non-limiting example, sensor 100 is used as an aid in a tool that is both size and cost constrained. In one embodiment, sensor 100 can be fitted in a cavity of a tool having a surface exposed or coupled to a component of the tool that opposes a surface to which a pressure or force is applied. For example, sensor 100 can be used in a dental drill to measure the pressure applied on a tooth thereby providing indication of an optimal pressure for removing material especially when the material is thin or delicate. The mechanical portion of sensor 100 comprises a stack of a first transducer, a medium, and an acoustically reflective surface. The stack can be made very thin depending on the application, the parameter to be measured, and the range of measurement. The small form factor allows it to be used on many existing devices that currently do not have sensing capability. Moreover, a non-continuous waveform pulsed sensing methodology is used to minimize power consumption. Power usage by sensor 100 can be made very low making it useful for devices having a temporary power source or battery operated devices.

In the example, sensor 100 can utilize more than one sensor stack. Using more than one sensor stack allows positional information to be provided. Sensor 100 can monitor where surface 106 of object 104 contacts the major surface of sensor 100. In one embodiment, the sensor stacks are in predetermined positions underlying the major surface of sensor 100. Force measurements in conjunction with the predetermined positions of each sensor stack is used to determine point or area contact by object 104 via force differentials. The electronics of sensor 100 can be within the sensor housing in or external to the sensor housing. In one embodiment, data from sensor 100 is transmitted to a receiving station 110 via wired or wireless communications. The receiving station 110 can include data processing, storage, or display, or combination thereof and provide real time graphical representation of the level and distribution of the load. Receiving station 110 can record and provide accounting information of sensor 100 to an appropriate authority. In a further embodiment, sensor 100 is a disposable system. Sensor 100 can be used as a low cost disposable measuring system that reduces capital expenditures, maintenance, and accounting when compared to permanent measurement systems.

Sensor 100 can measure forces (Fx, Fy, Fz) with corresponding locations and torques (e.g. Tx, Ty, and Tz) on the object 104 and the surface 102. The measured force and torque data is transmitted to receiving station 110 to provide real-time visualization for assisting the user in identifying any adjustments needed to achieve pressure and positioning. The data has substantial value in determining ranges of load and alignment tolerances required to minimize rework and optimize system performance.

Figure 2:
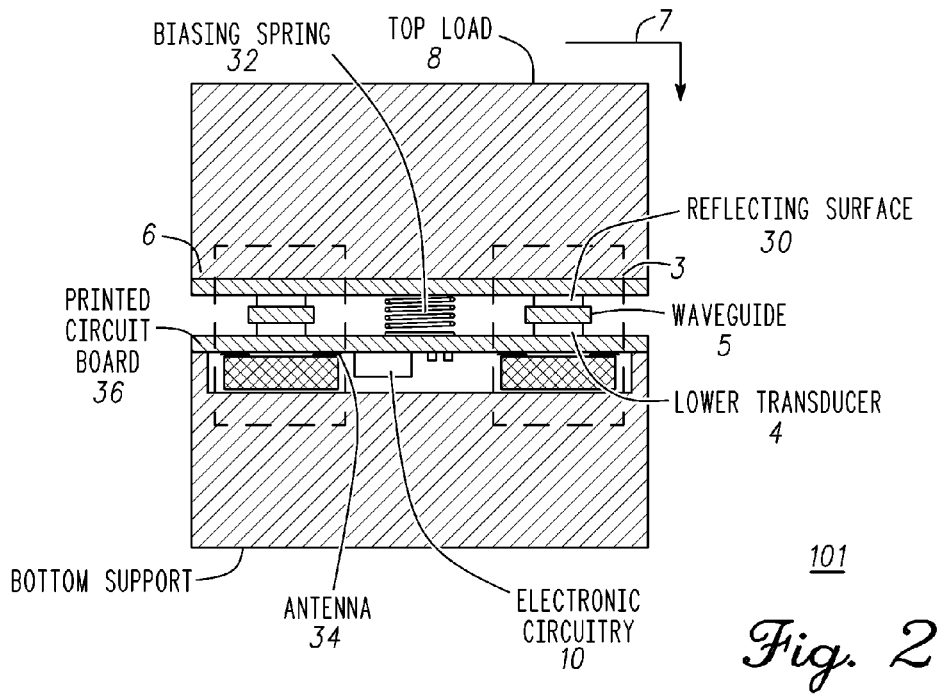
FIG. 2 is a simplified cross-sectional view of a sensing module in accordance with an exemplary embodiment.

FIG. 2 is a simplified cross-sectional view of a sensing module 101 (or assemblage) in accordance with an exemplary embodiment. The sensing module (or assemblage) is an electro-mechanical assembly comprising electrical components and mechanical components that when configured and operated in accordance with a sensing mode performs as a positive feedback closed-loop measurement system. The measurement system can precisely measure applied forces, such as loading, on the electro-mechanical assembly.

In one embodiment, the electrical components can include ultrasound resonators or transducers, ultrasound waveguides, and signal processing electronics, but are not limited to these. The mechanical components can include biasing springs 32, spring retainers and posts, and load platforms 6, but are not limited to these. The electrical components and mechanical components can be inter-assembled (or integrated) onto a printed circuit board 36 to operate as a coherent ultrasonic measurement system within sensing module 101 and according to the sensing mode. As will be explained hereinbelow in more detail, the signal processing electronics incorporate edge detect circuitry that detects an edge of a signal after it has propagated through waveguide 5. The detection initiates the generation of a new pulse by an ultrasound resonator or transducer that is coupled to waveguide 5 for propagation therethrough. A change in transit time of a pulse through waveguide 5 is measured and correlates to a change in material property of waveguide 5.

Sensing module 101 comprises one or more assemblages 3 each comprised one or more ultrasound resonators. As illustrated, waveguide 5 is coupled between transducers 4 and a reflective surface 30. In general, reflective surface 30 has a significant acoustic impedance mismatch suth tha a pulsed energy wave is reflected from surface 30. Very little of the pulsed energy wave is transmitted through reflective surface 30 due to the acoustic impedance mismatch. In a non-limiting example, reflective surface 30 can comprise materials such as a polymer, plastic, metal, or polycarbonate. In a non-limiting example, steel can be used as the metal. Transducer 4 and reflective surface 30 are affixed to a load bearing or contacting surfaces 6 to which an external condition is applied. In one exemplary embodiment, an ultrasound signal is coupled for propagation through waveguide 5. The sensing module 101 is placed, attached to, or affixed to, or within a body, instrument, or other physical system 7 having a member or members 8 in contact with the load bearing or contacting surfaces 6 of the sensing module 101. This arrangement facilitates translating the parameters of interest into changes in the length or compression or extension of the waveguide or waveguides 5 within the sensing module or device 100 and converting these changes in length into electrical signals. This facilitates capturing data, measuring parameters of interest and digitizing that data, and then subsequently communicating that data through antenna 34 to external equipment with minimal disturbance to the operation of the body, instrument, appliance, vehicle, equipment, or physical system 7 for a wide range of applications.

The sensing module 101 supports three modes of operation of pulse propagation and measurement: reflectance, unidirectional, and bi-directional. These modes can be used as appropriate for each individual application. In unidirectional and bi-directional modes, a chosen ultrasound resonator or transducer is controlled to emit pulses of ultrasound waves into the ultrasound waveguide and one or more other ultrasound resonators or transducers are controlled to detect the propagation of the pulses of ultrasound waves at a specified location or locations within the ultrasound waveguide. In reflectance or pulse-echo mode, a single ultrasound or transducer emits pulses of ultrasound waves into waveguide 5 and subsequently detects pulses of echo waves after reflection from a selected feature or termination of the waveguide. In pulse-echo mode, echoes of the pulses can be detected by controlling the actions of the emitting ultrasound resonator or transducer to alternate between emitting and detecting modes of operation. Pulse and pulse-echo modes of operation may require operation with more than one pulsed energy wave propagating within the waveguide at equilibrium.

Many parameters of interest within physical systems or bodies can be measured by evaluating changes in the transit time of energy pulses. The type and frequency of the energy pulse is determined by factors such as distance of measurement, medium in which the signal travels, accuracy required by the measurement, form factor of system, power constraints, and cost. In the non-limiting example, pulses of ultrasound energy provide accurate markers for measuring transit time of the pulses within waveguide 5. In general, an ultrasonic signal is an acoustic signal having a frequency above the human hearing range (e.g. >20 KHz). In one embodiment, a change in transit time of an ultrasonic energy pulse corresponds to a difference in the physical dimension of the waveguide from a previous state. For example, a force or pressure applied across the knee joint compresses wave guide 5 to a new length that is related to transit time of the energy pulse When integrated as a sensing module and inserted or coupled to a physical system or body, these changes are directly correlated to the physical changes on the system or body and can be readily measured as a pressure or a force.

Figure 3:
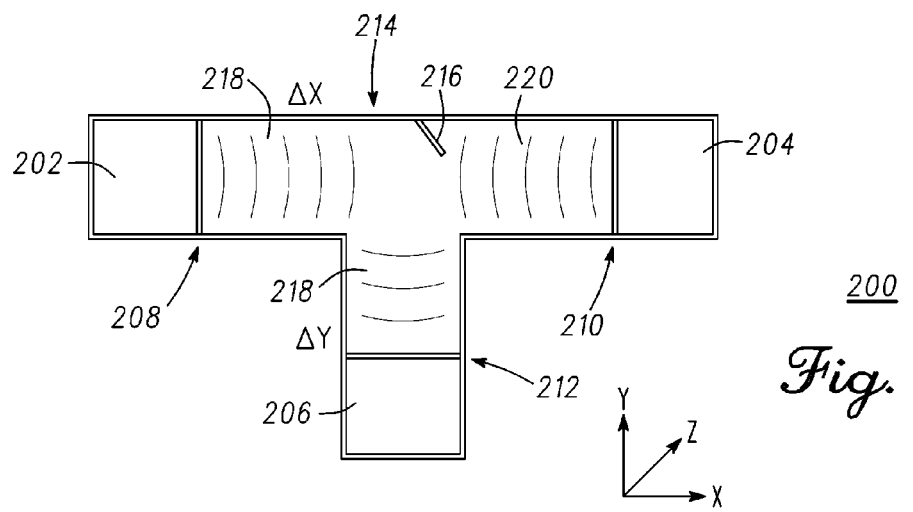
FIG. 3 is an exemplary assemblage for illustrating reflectance and unidirectional modes of operation.

FIG. 3 is an exemplary assemblage 200 for illustrating reflectance and unidirectional modes of operation. It comprises one or more transducers 202, 204, and 206, one or more waveguides 214, and one or more optional reflecting surfaces 216. The assemblage 200 illustrates propagation of ultrasound waves 218 within the waveguide 214 in the reflectance and unidirectional modes of operation. Either ultrasound resonator or transducer 202, 204, and 206 in combination with interfacing material or materials 208, 210, and 212 if required, can be selected to emit ultrasound waves 218 into the waveguide 214.

In unidirectional mode, either of the ultrasound resonators or transducers for example 202 can be enabled to emit ultrasound waves 218 into the waveguide 214. The non-emitting ultrasound resonator or transducer 204 is enabled to detect the ultrasound waves 218 emitted by the ultrasound resonator or transducer 202.

In reflectance mode, the ultrasound waves 218 are detected by the emitting ultrasound resonator or transducer after reflecting 220 from a surface, interface, or body at the opposite end of the waveguide 214. In this mode, either of the ultrasound resonators or transducers 202 or 204 can be selected to emit and detect ultrasound waves. Additional reflection features 216 can be added within the waveguide structure to reflect ultrasound waves. This can support operation in a combination of unidirectional and reflectance modes. In this mode of operation, one of the ultrasound resonators, for example resonator 202 is controlled to emit ultrasound waves 218 into the waveguide 214. Another ultrasound resonator or transducer 206 is controlled to detect the ultrasound waves 218 emitted by the emitting ultrasound resonator 202 (or transducer) subsequent to their reflection by reflecting feature 216.

Figure 4:
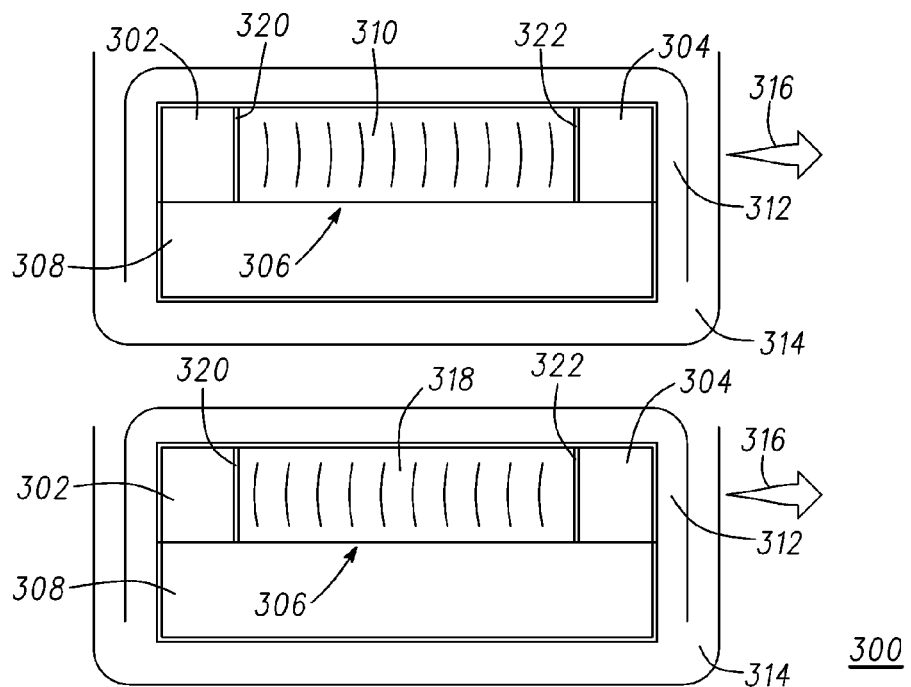
FIG. 4 is an exemplary assemblage that illustrates propagation of ultrasound waves within a waveguide in the bi-directional mode of operation of this assemblage.

FIG. 4 is an exemplary assemblage 300 that illustrates propagation of ultrasound waves 310 and 318 within the waveguide 306 in the bi-directional mode of operation of this assemblage. In this mode, the selection of the roles of the two individual ultrasound resonators (302, 304) or transducers affixed to interfacing material 320 and 322, if required, are periodically reversed. In the bi-directional mode, the transit time of ultrasound waves propagating in either direction within the waveguide 306 can be measured. This can enable adjustment for Doppler effects in applications where the sensing module 308 is operating while in motion 316. Furthermore, this mode of operation helps assure accurate measurement of the applied load, force, pressure, or displacement by capturing data for computing adjustments to offset this external motion 316. An advantage is provided in situations wherein the body, instrument, appliance, vehicle, equipment, or other physical system 314, is itself operating or moving during sensing of load, pressure, or displacement. Similarly, the capability can also correct in situation where the body, instrument, appliance, vehicle, equipment, or other physical system, is causing the portion 312 of the body, instrument, appliance, vehicle, equipment, or other physical system being measured to be in motion 316 during sensing of load, force, pressure, or displacement. Other adjustments to the measurement for physical changes to system 314 are contemplated and can be compensated for in a similar fashion. For example, temperature of system 314 can be measured and a lookup table or equation having a relationship of temperature versus transit time can be used to normalize measurements. Differential measurement techniques can also be used to cancel many types of common factors as is known in the art.

The use of waveguide 306 enables the construction of low cost sensing modules and devices over a wide range of sizes, including highly compact sensing modules, disposable modules for bio-medical applications, and devices, using standard components and manufacturing processes. The flexibility to construct sensing modules and devices with very high levels of measurement accuracy, repeatability, and resolution that can scale over a wide range of sizes enables sensing modules and devices to the tailored to fit and collect data on the physical parameter or parameters of interest a wide range of medical and non-medical applications.

For example, sensing modules or devices may be placed on or within, or attached or affixed to or within, a wide range of physical systems including, but not limited to instruments, appliances, vehicles, equipments, or other physical systems as well as animal and human bodies, for sensing the parameter or parameters of interest in real time without disturbing the operation of the body, instrument, appliance, vehicle, equipment, or physical system.

In addition to non-medical applications, examples of a wide range of potential medical applications may include, but are not limited to, implantable devices, modules within implantable devices, modules or devices within intra-operative implants or trial inserts, modules within inserted or ingested devices, modules within wearable devices, modules within handheld devices, modules within instruments, appliances, equipment, or accessories of all of these, or disposables within implants, trial inserts, inserted or ingested devices, wearable devices, handheld devices, instruments, appliances, equipment, or accessories to these devices, instruments, appliances, or equipment. Many physiological parameters within animal or human bodies may be measured including, but not limited to, loading within individual joints, bone density, movement, various parameters of interstitial fluids including, but not limited to, viscosity, pressure, and localized temperature with applications throughout the vascular, lymph, respiratory, and digestive systems, as well as within or affecting muscles, bones, joints, and soft tissue areas. For example, in orthopedic applications this may include, but is not limited to, load bearing prosthetic components, or provisional or trial prosthetic components for, but not limited to, surgical procedures for knees, hips, shoulders, elbows, wrists, ankles, and spines; any other orthopedic or musculoskeletal implant, or any combination of these.

Figure 5:
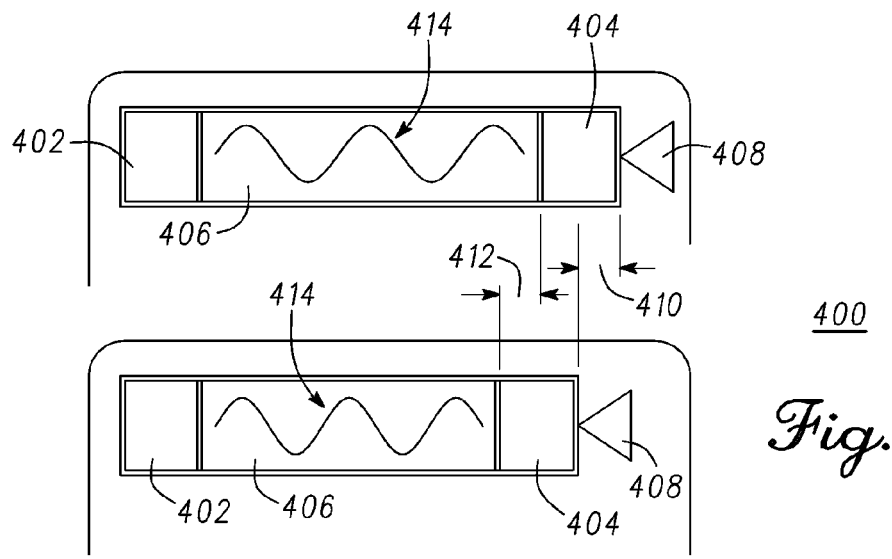
FIG. 5 is an exemplary cross-sectional view of a sensor element to illustrate changes in the propagation of ultrasound waves with changes in the length of a waveguide.

FIG. 5 is an exemplary cross-sectional view of a sensor element 400 to illustrate changes in the propagation of ultrasound waves 414 with changes in the length of a waveguide 406. In general, measurement of a parameter is achieved by relating displacement to the parameter. In one embodiment, the displacement required over the entire measurement range is measured in microns. For example, an external force 408 compresses waveguide 406 thereby changing the length of waveguide 406. Sensing circuitry (not shown) measures propagation characteristics of ultrasonic signals in the waveguide 406 to determine the change in the length of the waveguide 406. These changes in length change in direct proportion to the parameters of interest thus enabling the conversion of changes in the parameter or parameters of interest into electrical signals.

As illustrated, external force 408 compresses waveguide 406 and pushes the transducers 402 and 404 closer to one another by a distance 410. This changes the length 412 of the waveguide propagation path between transducers 402 and 404. Depending on the operating mode, the sensing circuitry measures the change in length of the waveguide 406 by analyzing characteristics of the propagation of ultrasound waves within the waveguide.

One interpretation of FIG. 5 illustrates waves emitting from transducer 402 at one end of waveguide 406 and propagating to transducer 404 at the other end of the waveguide 406. The interpretation includes the effect of movement of waveguide 406 and thus the velocity of waves propagating within waveguide 406 (without changing shape or width of individual waves) and therefore the transit time between transducers 402 and 404 at each end of the waveguide. The interpretation further includes the opposite effect on waves propagating in the opposite direction and is evaluated to estimate the velocity of the waveguide and remove it by averaging the transit time of waves propagating in both directions in turns, not simultaneously.

Changes in the parameter or parameters of interest are measured by measuring changes in the transit time of energy pulses or waves within the propagating medium. Closed loop measurement of changes in the parameter or parameters of interest is achieved by modulating the repetition rate of energy pulses or the frequency of energy waves as a function of the propagation characteristics of the elastic energy propagating structure.

These measurements may be implemented with an integrated wireless sensing module or device having an encapsulating structure that supports sensors and load bearing or contacting surfaces and an electronic assemblage that integrates a power supply, sensing elements, energy transducer or transducers and elastic energy propagating structure or structures, biasing spring or springs or other form of elastic members, an accelerometer, antennas and electronic circuitry that processes measurement data as well as controls all operations of ultrasound generation, propagation, and detection and wireless communications. The electronics assemblage also supports testability and calibration features that assure the quality, accuracy, and reliability of the completed wireless sensing module or device.

Figure 6:
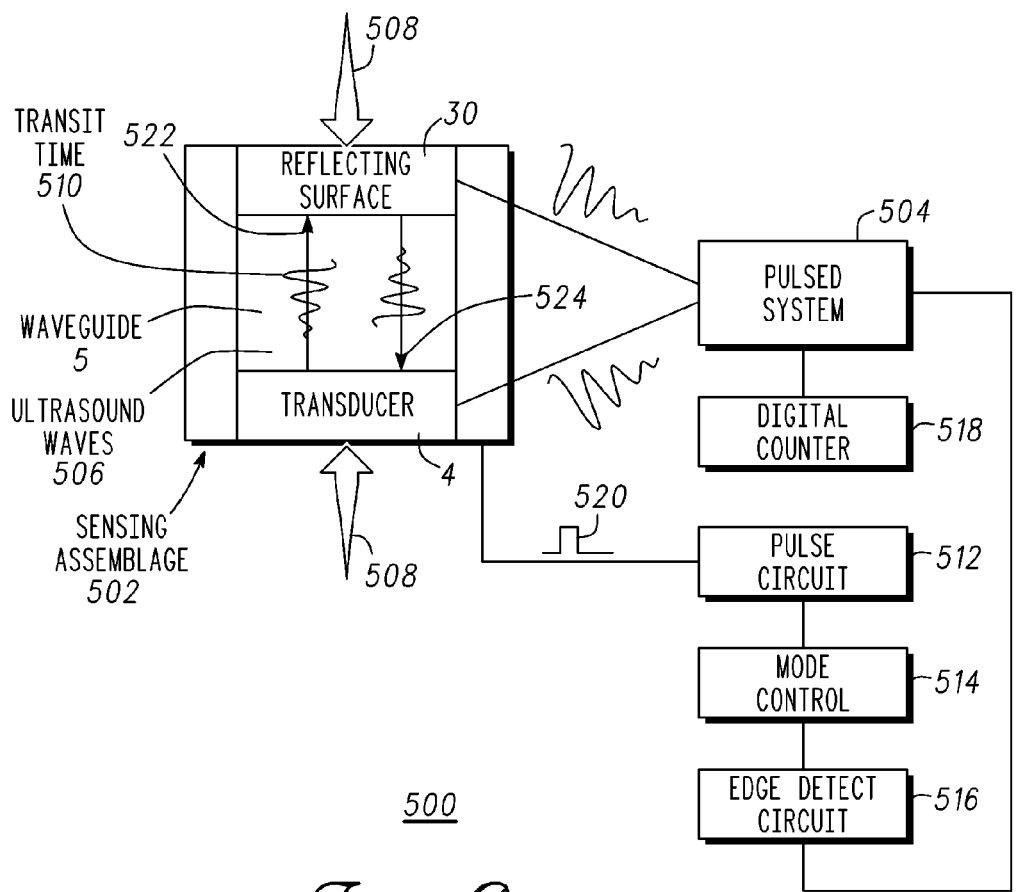
FIG. 6 is an exemplary block diagram of a measurement system in accordance with an exemplary embodiment.

FIG. 6 is an exemplary block diagram 500 of a measurement system in accordance with one embodiment. The measurement system comprises components of the sensing module 101 shown in FIG. 2. The measurement system includes a sensing assemblage 502 and a pulsed system 504 that detects energy waves 506 in one or more waveguides 5 of the sensing assembly 502. A pulse 520 is generated in response to the detection of energy waves 506 to initiate a propagation of a new pulse in waveguide 5.

The sensing assembly 502 comprises transducer 4, reflective surface 30, and a waveguide 5 (or energy propagating structure). In a non-limiting example, sensing assemblage 502 is affixed to load bearing or contacting surfaces 508. External forces or conditions for measurement are applied to the contacting surfaces 508. In at least one exemplary embodiment, the external forces 508 compress the waveguide 5 thereby changing the length of the waveguide 5 depending on the force applied thereon. Similarly, transducer 4 and reflective surface 30 also move closer together under compression. In the reflected or pulsed echo mode, a transit time 510 of a pulsed energy wave comprises a time period indicated by arrow 522 of the pulsed energy wave moving from transducer 4 through waveguide 5 to reflective surface 30 plus the echo time period indicated by arrow 524 comprising a reflected pulse energy wave moving from reflective surface 30 through waveguide 5 back to transducer 4. Thus, a change in length of waveguide 5 affects the transit time 510 of energy waves 506 comprising the transmitted and reflected path. The pulsed system 504 in response to a physical change that shortens the length of waveguide 5 will detect each energy wave sooner (e.g. shorter transit time) and initiate the propagation of new pulses associated with a corresponding shorter transit time. As will be explained below, this is accomplished by way of pulse system 504 in conjunction with the pulse circuit 512, the mode control 514, and the edge detect circuit 516.

Notably, changes in the waveguide 5 (energy propagating structure or structures) alter the propagation properties of the medium of propagation (e.g. transmit time 510). A pulsed approach reduces power dissipation allowing for a temporary power source such as a battery or capacitor to power the system during the course of operation. In at least one exemplary embodiment, a pulse is provided to transducer 4 coupled to a first surface of waveguide 5. Transducer 4 generates a pulsed energy wave 506 coupled into waveguide 5. In a non-limiting example, transducer 4 is a piezo-electric device capable of transmitting and receiving acoustic signals in the ultrasonic frequency range. Transducer 4 is toggled between an emitting mode to emit a pulsed energy wave into waveguide 5 and a receiving mode to generate an electrical signal corresponding to a reflected pulsed energy wave.

In a start up mode, transducer 4 is enabled for receiving the reflected pulsed energy wave after generating one or more pulsed energy waves and delivering them into waveguide 5. Upon receiving the reflected pulsed energy wave, transducer 4 generates an electrical signal corresponding to the reflected pulsed energy wave. The electrical signal output by transducer 4 is coupled to edge detect circuit 516. In at least one exemplary embodiment, edge detect circuit 516 detects a leading edge of the electrical signal output by transducer 4 (e.g. the propagated reflected energy wave 506). The detection of the reflected propagated pulsed signal occurs earlier (due to the length/distance reduction of waveguide 5) than a prior signal due to external forces 508 being applied to compress sensing assemblage 502. Pulse circuit 512 generates a new pulse in response to detection of the propagated and reflected pulsed signal by edge detect circuit 516. Transducer 4 is then enabled to generate a new pulsed energy wave. A pulse from pulse circuit 512 is provided to transducer 4 to initiate a new pulsed sequence. Thus, each pulsed sequence is an event of pulse propagation, pulse detection and subsequent pulse generation that initiates the next pulse sequence.

The transit time 510 of the propagated pulse is the total time it takes for a pulsed energy wave to travel from transducer 4 to reflecting surface 30 and from reflecting surface 30 back to transducer 4. There is delay associated with each circuit described above. Typically, the total delay of the circuitry is less than the propagation time of a pulsed signal through waveguide 5. Multiple pulse to pulse timings can be used to generate an average time period when change in external forces 508 occur relatively slowly in relation to the pulsed signal propagation time. The digital counter 518 in conjunction with electronic components counts the number of propagated pulses to determine a corresponding change in the length of the waveguide 5. These changes in length change in direct proportion to the external force thus enabling the conversion of changes in parameter or parameters of interest into electrical signals.

One method of operation holds the number of pulsed energy waves propagating through waveguide 5 as a constant integer number. A time period of a pulsed energy wave corresponds to the time between the leading pulse edges of adjacent pulsed energy waves. A stable time period or a period of equilibrium is one in which the time period changes very little over a number of pulsed energy waves. This occurs when conditions that affect sensing assemblage 502 stay consistent or constant. Holding the number of pulsed energy waves propagating through waveguide 5 to an integer number is a constraint that forces a change in the time between pulses when the length of waveguide 5 changes. The resulting change in time period of each pulsed energy wave corresponds to a change in aggregate pulse periods that can be captured using digital counter 518 and correlated to a measurement of external forces or conditions 508.

In an alternate embodiment, the repetition rate of pulsed energy waves 506 emitted by transducer 4 can be controlled by pulse circuit 512. The operation remains similar where the parameter to be measured corresponds to the measurement of the transit time 510 of pulsed energy waves 506 within waveguide 5 as described above. It should be noted that an individual ultrasonic pulse can comprise one or more energy waves with a damping wave shape as shown. The pulsed energy wave shape is determined by the electrical and mechanical parameters of pulse circuit 512, interface material or materials, where required, and ultrasound resonator or transducer 4. The frequency of the pulsed energy waves is determined by the response of the emitting ultrasound resonator 4 to excitation by an electrical pulse 520. The mode of the propagation of the pulsed energy waves 506 through waveguide 5 is controlled by mode control circuitry 514 (e.g., reflectance or uni-directional). The detecting ultrasound resonator or transducer may either be a separate ultrasound resonator or the emitting resonator or transducer 4 depending on the selected mode of propagation (reflectance or unidirectional).

In general, accurate measurement of physical parameters is achieved at an equilibrium point having the property that an integer number of pulses are propagating through the energy propagating structure at any point in time. Measurement of changes in the "time-of-flight" or transit time of ultrasound pulses within a waveguide of known length can be achieved by modulating the repetition rate of the ultrasound pulses as a function of changes in distance or velocity through the medium of propagation, or a combination of changes in distance and velocity, caused by changes in the parameter or parameters of interest.

It should be noted that ultrasound energy pulses or waves, the emission of ultrasound pulses or waves by ultrasound resonators or transducers, transmitted through ultrasound waveguides, and detected by ultrasound resonators or transducers are used merely as examples of energy pulses, waves, and propagation structures and media. Other embodiments herein contemplated can utilize other wave forms, such as, light.

Measurement by pulsed system 504 and sensing assemblage 502 enables high sensitivity and signal-to-noise ratio as the time-based measurements are largely insensitive to most sources of error that may influence voltage or current driven sensing methods and devices. The resulting changes in the transit time of operation corresponds to frequency which can be measured rapidly and with high resolution. This achieves the required measurement accuracy and precision thus capturing changes in the physical parameters of interest and enabling analysis of their dynamic and static behavior.

Figure 7:
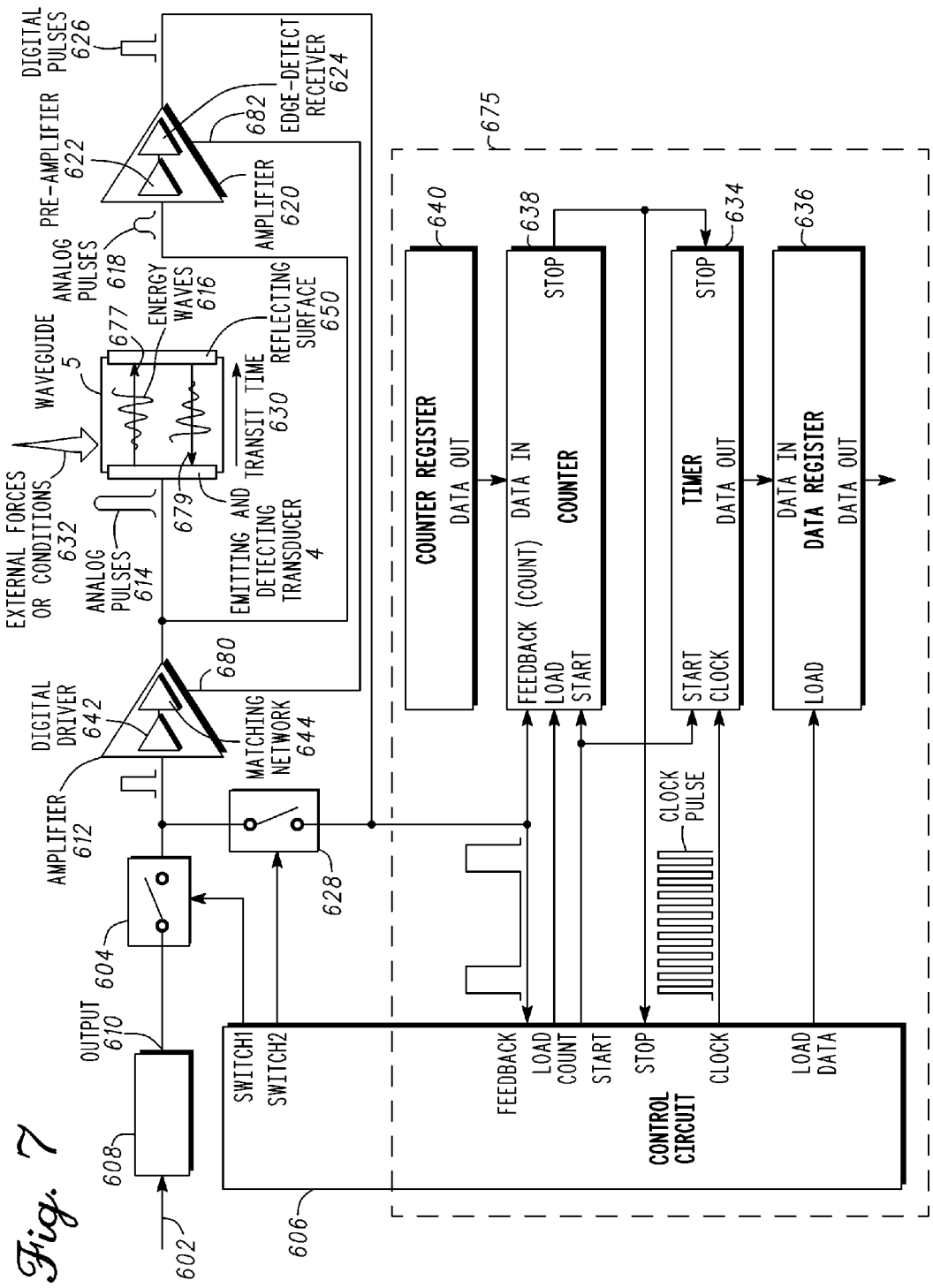
FIG. 7 is measurement system operating in a pulsed echo mode with digital output according to one embodiment.

FIG. 7 is a measurement system operating in pulsed echo mode with digital output according to one embodiment. In particular, it illustrates a measurement sequence comprising pulse emission into a medium, propagation through the medium, reflection, detection of the reflected propagated signal, and measurement of the transit time. The medium is subjected to the parameter to be measured such as weight, strain, pressure, wear, vibration, viscosity, and density. In a non-limiting example, pressure is a parameter used to illustrate the measurement system. Pressure is applied across the medium in a direction of the traversed path of the waveform. The pressure compresses the medium thereby changing the length of the medium. In general, reducing the length of the traversed path by the pulse correspondingly lowers the transit time of the waveform. The transit time is correlated to a pressure measurement in conjunction with the material properties of the medium. In one embodiment, the transit time is converted to a length, or change in length, of the medium at the time of the measurement. The material properties of the medium are known where a mathematical function or look up table correlates force or pressure to the measured length or change in length. Further accuracy can be obtained by including any other external conditions (ex. temperature) that affect the medium at the time of the measurement.

The system allows for more than one than one measurement to be taken. In one embodiment, a new measurement sequence is initiated upon detecting a propagated waveform. A pulse is generated upon detection of the propagated pulsed energy wave. The pulse is provided to transducer 4 to emit a new pulsed energy wave into the medium. The process continues until stopped under user control. The system provides the benefit of very low power usage because as little as a single pulsed energy wave can be used to make a measurement whereas a continuous wave measurement requires a continuous signal to be maintained. Reducing the pulse width can also lower power usage since only the leading edge is being detected. A further benefit is that in a low power application a high energy pulsed wave can be used to compensate for attenuation in the medium or a significant distance of travel. Although attenuated by the medium, the measurement can be highly accurate and the signal detectable. The high-energy pulse would be difficult to sustain in low power environment (e.g. battery or temporary power source) but in pulsed mode can be used to make measurements that would be difficult using other methodologies.

Referring to FIG. 2, in pulse echo mode of operation, the sensing module 101 measures a time of flight (TOF) between when a pulsed energy wave is transmitted by transducer 4 into waveguide 5, reflected, and received by transducer 4. Transducer 4 generates a signal corresponding to the received reflected pulse. The time of flight determines the length of the waveguide propagating path, and accordingly reveals the change in length of the waveguide 5. In another arrangement, differential time of flight measurements can be used to determine the change in length of the waveguide 5. A pulse can comprise a pulse of one or more waves. The waves may have equal amplitude and frequency (square wave pulse) or they may have different amplitudes, for example, decaying amplitude (trapezoidal pulse) or some other complex waveform. The pulsed system detects an edge of each pulse propagating through the waveguide and holds the delay between each edge constant under stable operating conditions.

A pulse method facilitates separation of ultrasound frequency, damping waveform shape, and repetition rate of pulses of ultrasound waves. Separating ultrasound frequency, damping waveform shape, and repetition rate enables operation of ultrasound transducers at or near resonance to achieve higher levels of conversion efficiency and power output thus achieving efficient conversion of ultrasound energy. This may enable, but is not limited to, lower power operation for ultra-low power devices.

The operation of the measurement system will be described utilizing the timing diagram of FIG. 8. In general, one or more pulsed energy waves can be propagating through the medium during a measurement. In a non-limiting example, a measurement sequence comprises a single ultrasonic pulsed energy wave emitted into propagating structure or waveguide 5, propagation through waveguide 5, reflection off a reflecting surface 650, propagation through waveguide 5, and detection by transducer 4. In at least one exemplary embodiment, the system maintains an integer number of pulses within waveguide 5 while the time period of a pulsed energy wave varies due to external forces or conditions 632 applied to the propagating medium. In one embodiment, external forces or conditions 632 are applied to lengthen or shorten a propagating path of the pulsed energy waves. The time period of each pulsed energy wave remains constant when multiple measurements are taken and conditions 632 do not vary.

The measurement system comprises a pulse circuit 608, a switch 604, an amplifier 612, a transducer 4, a waveguide 5, a reflecting surface 650, an amplifier 620, a switch 628, and a digital logic circuit 675. Control circuitry 606 can be part of digital logic circuit 675. Switch 604 has a first terminal coupled to an output 610 of pulse circuit 608, a control terminal, and a second terminal. Amplifier 612 has an input coupled to the second terminal of switch 604, a control output 680, and an output. Transducer 4 has a terminal coupled to the output of amplifier 612 and is operatively coupled for emitting a pulsed energy wave to waveguide 5 at a first location of waveguide 5. Reflecting surface 650 is operatively coupled for reflecting a pulsed energy wave propagated through waveguide 5 at a second location. Reflecting surface 650 is not transmissive to pulsed energy waves and typically represents a high acoustic mismatch that promotes reflectivity. Thus, transducer 4 both emits pulsed energy waves into waveguide 5 and generates a signal corresponding the received reflected pulsed energy waves at the first location. Amplifier 620 has an input coupled the terminal of transducer 4, a control input 682 coupled to the control output 680 of amplifier 612, and an output. Switch 628 has a first terminal coupled to the output of amplifier 620, a control terminal, and a second terminal coupled to the input of amplifier 612. Digital logic circuit 675 has one or more outputs for initiating a sensing sequence, taking multiple measurements, and measuring the transit time or time period of propagated pulsed energy waves.

Transducer 4 has two modes of operation. Transducer 4 emits a pulsed energy wave into medium 5. Transducer 4 is then enabled to receive and generate a signal corresponding to a reflected pulsed energy wave reaching the second location. Upon receiving the reflected pulse energy wave transducer 4 converts the reflected pulsed energy wave into analog pulses 618 of electrical waves having the same repetition rate. Transducer 4 then is enabled to emit a new pulsed energy wave. Thus, transducer 4 is used in a repeating sequence of emitting and detecting. The analog pulses 618 output by transducer 4 (in the reflected pulse receiving mode) may need amplification.

The timing diagram of FIG. 8 will be referred to in description of pulse echo mode operation of the measurement system hereinbelow. In particular, pressure or force is measured as an illustration of a parameter being measured. Control circuit 606 initiates a measurement sequence by providing control signals to switches 604 and 628 respectively indicated by closed position 842 and open position 846 of FIG. 8. Pulse circuit 608 can then be enabled to provide one or more ultrasonic pulsed energy waves to amplifier 612. In the example disclosed above, at least one pulse will be provided by pulse circuit 608 to initiate one or more measurement. In FIG. 8, pulse circuit 608 provides pulses 802, 804, 806, and 808 to amplifier 612. It should be noted that pulses 804, 806, and 808 are not needed if pulse 802 results in a detection and subsequent pulse generation by amplifier 620. In general, the an integer number of pulses can be propagating through waveguide 5. As shown in FIG. 8, a single pulse propagates through waveguide 5 at any point in time. The time period of the pulsed energy wave is equal to or less than the transit time to traverse waveguide 5 twice.

Amplifier 612 receives the pulses from pulse circuit 608 and provides analog pulses 614 to the terminal of transducer 4. In at least one exemplary embodiment amplifier 612 comprises a digital driver 642 and matching network 644. Digital driver 642 and matching network 644 transforms the digital output (e.g. square wave) of pulse circuit 608 into shaped or analog pulses 614 that are modified for emitting transducer 4. The repetition rate of pulses 614 is equal to the repetition rate of the pulses provided by pulse circuit 612. Amplifier 612 drives transducer 4 with sufficient power to generate energy waves 616. In a non-limiting example, energy waves 616 propagating through waveguide 5 are ultrasound waves.

In general, ultrasound transducers naturally resonate at a predetermined frequency. Providing a square wave or digital pulse to the terminal of emitting transducer 4 could yield undesirable results. Digital driver 642 of amplifier 612 drives matching network 644. Matching network 644 is optimized to match an input impedance of emitting transducer 4 for efficient power transfer. In at least one exemplary embodiment, digital driver 642, matching network 644, solely, or in combination shapes or filters pulses provided to the input of amplifier 612. The waveform is modified from a square wave to analog pulse 614 to minimize ringing and to aid in the generation of a damped waveform by emitting transducer 4. The rounded pulses illustrated in FIG. 8 at the output of amplifier 612 are representative of the pulse modification. In one embodiment, a pulsed energy wave emitted into waveguide 5 can ring with a damped envelope that affects signal detection, which will be disclosed in more detail below.

The one or more pulsed energy waves 616 are emitted at a first location of waveguide 5, propagate through energy propagating structure or waveguide 5, are reflected by reflecting surface 650, propagate back towards the first surface, and then are detected by transducer 4 at the first location. In the example, a pulsed energy wave 820 of FIG. 8 is generated by transducer 4 by pulse 802 from pulse circuit 608. Pulsed energy wave 820 propagates in waveguide 5 from the first location towards reflecting surface 650 and back to transducer 4 after being reflected. The pulsed energy wave 820 of FIG. 8 is detected by transducer 4 upon reaching the first location. Transducer 4 generates a signal corresponding to the received pulsed energy wave 820 that is coupled to the input of amplifier 620. In general, detecting transducer 4 converts propagated pulsed energy waves 616 into pulses 618 of electrical waves having the same repetition rate. The signal output of detecting transducer 4 may need amplification.

Amplifier 620 comprises pre-amplifier 622 and edge-detect receiver 624. In a first mode, amplifier 620 receives a control signal from amplifier 612 to blank, disable, or decouple the output of amplifier 620 when transducer 4 is emitting a pulsed energy wave into waveguide 5. The control signal is provided from control output 680 of amplifier 612 to control input 682 of amplifier 620. In a second mode, the control signal from amplifier 612 enables the output for providing a signal to transducer 4. Pre-amplifier 622 receives and amplifies analog pulses 618 from transducer 4 in the second mode. Amplifier 620 toggles between the first and second modes of operation depending on whether transducer 4 is emitting or receiving a pulsed energy wave. Edge-detect receiver 624 detects an edge of each arriving pulse corresponding to each propagated pulsed energy wave 616 through waveguide 5. As mentioned previously, each pulsed energy wave can be a ringing damped waveform. In at least one exemplary embodiment, edge-detect receiver 624 detects a leading edge of each arriving pulse 618. Edge-detect receiver 624 can have a threshold such that signals below the threshold cannot be detected. Edge-detect receiver 624 can include a sample and hold that prevents triggering on subsequent edges of a ringing damped signal. The sample and hold can be designed to "hold" for a period of time where the damped signal will fall below the threshold but less than the time period between adjacent pulses under all operating conditions.

Amplifier 620 generates a digital pulse 626 that is triggered by each leading edge of each propagated pulsed energy waves 616 detected by transducer 4. The first digital pulse output by amplifier 626 is indicated by pulse 810 of FIG. 8. Pulse 810 corresponds to pulsed energy wave 822 of FIG. 8. In a non-limiting example, control circuitry 606 responds to the first digital pulse output from amplifier 620 after starting a measurement sequence by closing switch 628 and opening switch 604. The control signals for switches 604 and 628 are respectively indicated by control signal 844 and 848. Pulses 804, 806, and 808 of FIG. 8 output by pulse circuit 608 are not received by amplifier 612 after switch 604 opens.

A positive feedback closed loop circuit is then formed that couples a pulse generated by amplifier 620 to the input of amplifier 612 thereby sustaining a sequence comprising: a pulsed energy wave emission into waveguide 5 at the first location; propagation of the pulsed energy wave 616 through waveguide 5; reflection of the pulsed energy waves 616 by reflecting surface 650 at the second location; propagation of the pulse energy waves 616 back to the first location; detection and signal generation of the pulsed energy waves 616 by transducer 4; and generation of a digital pulses 626 by amplifier 620. Each digital pulse 626 is of sufficient length to sustain the pulse behavior of the measurement system when it is coupled back to amplifier 612 through switch 628. Alternatively, a measurement process can be stopped by opening switches 604 and 628 such that no pulses are provided to amplifier 612 and thereby to transducer 4. In general, circuitry of the measurement system that dissipates power can be turned off or put into a sleep mode when decoupled from amplifier 612 by switches 604 and 628.

In one embodiment, the delay of amplifiers 620 and 612 is small in comparison to the propagation time of a pulsed energy wave through waveguide 5. In an equilibrium state, an integer number of pulses of energy waves 616 in waveguide 5 have equal time periods and transit times when propagating through energy propagating structure or waveguide 5. In general, as one energy pulse wave is detected by transducer 4, a new energy pulse wave is emitted into waveguide 5 (after some finite delay). Transit time 854 is the time required for a pulsed energy wave to traverse waveguide 5 twice. A time period 852 is the time between pulses. In the single pulse example, time period 852 and transit time 854 are similar or equal. The time period 852 is less than the transit time 864 when more than one pulsed energy waves reside within waveguide 5 simultaneously. Movement or changes in the physical properties of the energy propagating structure or waveguide 5 change the transit time 630 of energy waves 616. This disrupts the equilibrium thereby changing when a pulsed energy wave is detected by edge-detect receiver 624. A transit time 854 is reduced should external forces 632 compress waveguide 5 in the direction of propagation of energy waves 616. Conversely, the transit time is increased should external forces 632 result in waveguide 5 expanding in length. The change in transit time delivers digital pulses 626 earlier or later than previous pulses thereby producing an adjustment to the delivery of analog pulses 618 and 614 to a new equilibrium point. The new equilibrium point will correspond to a different transit time (e.g. different frequency) but the same integer number of pulses.

Shown in FIG. 8 are pulses 822, 824, 826 and 828 that are emitted into waveguide 5 by transducer 4 after switch 628 is closed. Transducer 4 emits pulses 822, 824, 826, and 830 in response to pulses 810, 812, 814, and 816 output by amplifier 820 that respectively correspond to the detection of propagated pulsed energy waves 820, 822, 824, and 826 of FIG. 8 that have been reflected back to the first location. Although only four pulsed energy waves are shown in FIG. 8, they will continue to be emitted into waveguide 5 for measurement as long as switch 628 remains closed. The transit time 854 of pulses 820, 822, 824, 826, and 828 correspond to the parameter being measured (e.g. force or pressure in the example). Switch 604 closes and switch 628 opens after pulse 816 thereby breaking the positive closed loop feedback. Transducer 4 does not emit any pulsed energy waves until pulse circuit 608 initiates another measurement sequence.

In one embodiment, transit time 630 of each pulse can be measured by digital logic circuit 675 using a high-speed clock and a counter. For example, an edge of analog pulse 614 provided to transducer 4 can initiate a count by the high-speed clock. The generation of a digital pulse 624 can stop the count and store the number in memory. The count is multiplied by the time period of a clock cycle, which will correspond to the transit time of the pulsed energy wave. The clock can be reset for the next measurement sequence in response to the digital pulse 624. A similar approach can be deployed measuring a time period of a pulse to pulse output by amplifier 620.

As previously disclosed, the repetition rate of energy waves 616 during operation of the closed loop circuit, and changes in this repetition rate, can be used to measure changes in the movement or changes in the physical attributes of energy propagating structure or medium 5. The changes can be imposed on the energy propagating structure or medium 5 by external forces or conditions 632 thus translating the levels and changes of the parameter or parameters of interest into signals that may be digitized for subsequent processing, storage, and display. Thus, the repetition rate of pulses of energy waves 616 can be related to a pulsed energy wave time period of single pulsed energy wave or over multiple pulsed energy wave time periods during the operation of the closed loop circuit, and changes in this repetition rate, can be used to measure movement or changes in physical attributes of energy propagating structure or medium 5.

The changes in physical attributes of energy propagating structure or medium 5 by external forces or conditions 632 translates the levels and modifies the parameter or parameters of interest into a time period difference of adjacent pulses, a time period difference of transit time, or a difference accumulated or averaged over multiple time periods for the pulsed energy wave time period or transit time. The time period or transit time corresponds to a frequency for the time period measured. The new frequency can be digitized for subsequent transmission, processing, storage, and display. Translation of the measured frequency into digital binary numbers facilitates communication, additional processing, storage, and display of information about the level and changes in physical parameters of interest. Prior to measurement of the frequency, control logic 606 loads the loop count into digital counter 634 that is stored in digital register 636.

Digital logic circuit 675 is described in more detail hereinbelow. As previously mentioned, a first pulse at output 610 from pulse circuit 608 initiates a parameter measurement or sensing of waveguide 5. In at least one exemplary embodiment, sensing does not occur until initial equilibrium has been established. Alternatively, each time period of a pulsed energy wave or transit time period 630 of the pulsed energy wave can be measured and reviewed. Thus, each pulse energy wave detection and generation of a digital pulse can be a separate and unique event. Control circuit 606 detects digital pulses 626 from amplifier 620 (closing switch 628 and opening switch 604) to establish equilibrium and start measurement operations. In an extended configuration of pulse echo mode, a digital block is coupled to the pulsed echo mode measurement system for digitizing the frequency of operation. Translation of the time period of pulsed energy waves into frequency (digital binary numbers) facilitates communication, additional processing, storage, and display of information about the level and changes in physical parameters of interest. During this process, control circuit 606 enables digital counter 638 and digital timer 634. Digital counter 638 decrements its value on the rising edge of each digital pulse output by amplifier 620. In one embodiment, digital timer 634 increments its value on each rising edge of pulses from a clock circuit. A clock such as a crystal oscillator is used to clock digital logic circuit 675 and as a reference in which to gauge time periods of pulsed energy waves. Alternatively, pulse circuit 608 can be a reference clock. When the number of digital pulses 626 has decremented, the value within digital counter 638 to zero a stop signal is output from digital counter 638. The stop signal disables digital timer 634 and triggers control logic 606 to output a load command to data register 636. Data register 636 loads a binary number from digital timer 634 that is equal to the period of the energy waves or pulses times the value in counter 638 divided by a clock period corresponding to oscillator output 610. With a constant clock period, the value in data register 636 is directly proportional to the aggregate period of the pulsed energy waves or pulses accumulated during the measurement operation. Duration of the measurement operation and the resolution of measurements may be adjusted by increasing or decreasing the value preset in the count register 640.

This method of operation further enables setting the level of precision or resolution of the captured data by using long cycle counts to optimize trade-offs between measurement resolution versus pulse repetition rate, ultrasound frequency, and damping waveform shape, as well as the bandwidth of the sensing and the speed of the data processing operations to achieve an optimal operating point for a sensing module or device that matches the operating conditions of the system containing, or subject to, the parameter or parameters of interest.

In at least one exemplary embodiment, the sensor system includes the system as a wireless module that operates according to one or more criteria such as, but not limited to, power level, applied force level, standby mode, application context, temperature, or other parameter level. Pulse shaping can also be applied to increase reception quality depending on the operational criteria. The wireless sensing module comprises the pulsed measurement system, one or more sensing assemblies, one or more load surfaces, an accelerometer, electronic circuitry, a transceiver, and an energy supply. The wireless sensing module measures a parameter such as force/pressure and transmits the measurement data to a secondary system for further processing and display. The electronic circuitry in conjunction with the sensing assemblies accurately measures physical displacements of the load surfaces on the order of a few microns more or less along various physical dimensions. The sensing assembly physically changes in response to an applied force, such as an applied load. Electronic circuitry operating in a positive feedback closed-loop circuit configuration precisely measures changes in propagation time due to changes in the length of the waveguides; physical length changes which occur in direct proportion to the applied force.

In a non-limiting example, an ultrasound signal is used in the measurement system. For illustration purposes, the measurement system measures a load, pressure, or force. The system has two surfaces to which the measured parameter (e.g. load, pressure, force) can be applied. In one embodiment, one of the surfaces is in a fixed position and the measured parameter is applied to the remaining surface. Alternatively, the measured parameter can be applied across both surfaces. In one embodiment, the system will measure within a range of 3-60 pounds.

The sensing element comprises a piezoelectric transducer, a medium, and a reflective surface. One or more sensing elements can be used. The sensing element is placed between the surfaces of the measurement system. In one embodiment, the waveguide comprises a polymer such as urethane or polyethylene. In a non-limiting example, the polymer can be stretched or compressed when subjected to the parameter under measurement and the system has little or no hysteresis. The waveguide efficiently contains and directs an ultrasonic pulsed energy wave such that a measurement of either the transit time of the pulsed energy wave to propagate through the waveguide or time period of the pulsed energy wave can be taken. The waveguide can be cylindrically shaped having a first end and a second end of the cylinder. The piezoelectric transducers are attached at the first and second ends of the waveguide to emit and receive ultrasonic pulsed energy waves. The transducers are attached to be acoustically coupled the waveguide and can have an intermediate material layer to aid in improving the transfer of the ultrasonic pulsed energy wave.

In the non-limiting example, the waveguide in a relaxed state is a cylinder or column 47 millimeters long, which can accommodate one, or more ultrasonic pulsed energy waves. The length of the waveguide corresponds to the thickness of the sensor and is thus an indication that a very small form factor sensor can be built using this methodology. In one embodiment, the waveguide is placed in a compressed state in the sensor module. In the non-limiting example, the waveguide is subjected to a force or pressure that changes the dimensions of the cylinder. More specifically, an applied force or pressure on the surfaces of the system modifies the length of the waveguide. In one embodiment, the waveguide is compressed from the 47 millimeter relaxed state to a thickness of approximately 39 millimeters. The 39 millimeter compressed state corresponds to the state where no load is applied to the surfaces of the sensor module.

In the non-limiting example, the emitting piezoelectric transducer has a different resonant frequency than the receiving piezoelectric transducer. The emitting piezoelectric transducer has a resonance frequency of approximately 8 megahertz. It has a diameter of approximately 3.3 millimeters and is approximately 0.23 millimeters thick. The receiving piezoelectric transducer has a resonance frequency of approximately 10-13 megahertz. It has a diameter of 4 millimeters and is approximately 0.17 millimeters. In one embodiment, the waveguide has a diameter greater than or equal to the diameter of the largest piezoelectric transducer. In the example, the waveguide would have a diameter greater than or equal to 4 millimeters.

The sensing module can very accurately measure transit time or a time period of the pulsed energy wave as disclosed hereinabove. In at least one exemplary embodiment, a single pulsed energy wave can be used to take a measurement thereby minimizing energy usage. Alternatively, more than one measurement can be taken sequentially, periodically, or randomly depending on the application requirements. The measured transit time or time period corresponds to the length of the medium or waveguide. The transit time or time period is correlated to a force or pressure required to compress the waveguide by the measured amount. Preliminary measurements indicate that the sensing module can detect changes in the length of the waveguide on the order of submicrons. Thus, the sensing module can measure the force or changes in force with high precision.

Upon reviewing the aforementioned embodiments, it would be evident to an artisan with ordinary skill in the art that said embodiments could be modified, reduced, or enhanced without departing from the scope and spirit of the claims described below. As an example:

Changing repetition rate of complex waveforms to measure time delays.

Changing repetition rate of acoustical, sonic, or light, ultraviolet, infrared, RF or other electromagnetic waves, pulses, or echoes of pulses to measure changes in the parameter or parameters of interest.

FIG. 9 is an exemplary block diagram of the components of a sensing module. It should be noted that the sensing module could comprise more or less than the number of components shown. As illustrated, the sensing module includes one or more sensing assemblages 903, a transceiver 920, an energy storage 930, electronic circuitry 907, one or more mechanical supports 915 (e.g., springs), and an accelerometer 902. In the non-limiting example, an applied compressive force can be measured by the sensing module.

The sensing assemblage 903 can be positioned, engaged, attached, or affixed to the contact surfaces 906. Mechanical supports 915 serve to provide proper balancing of contact surfaces 906. In at least one exemplary embodiment, contact surfaces 906 are load-bearing surfaces. In general, the propagation structure 905 is subject to the parameter being measured. Surfaces 906 can move and tilt with changes in applied load; actions which can be transferred to the sensing assemblages 903 and measured by the electronic circuitry 907. The electronic circuitry 907 measures physical changes in the sensing assemblage 903 to determine parameters of interest, for example a level, distribution and direction of forces acting on the contact surfaces 906. In general, the sensing module is powered by the energy storage 930.

As one example, the sensing assemblage 903 can comprise an elastic or compressible propagation structure 905 between a transducer 904 and a reflective surface 914. In the current example, transducer 904 can be an ultrasound (or ultrasonic) resonator, and the elastic or compressible propagation structure 905 can be an ultrasound (or ultrasonic) waveguide (or waveguides). The electronic circuitry 907 is electrically coupled to the sensing assemblages 903 and translates changes in the length (or compression or extension) of the sensing assemblages 903 to parameters of interest, such as force. It measures a change in the length of the propagation structure 905 (e.g., waveguide) responsive to an applied force and converts this change into electrical signals which can be transmitted via the transceiver 920 to convey a level and a direction of the applied force. In other arrangements herein contemplated, the sensing assemblage 903 may require only a single transducer. In yet other arrangements, the sensing assemblage 903 can include piezoelectric, capacitive, optical or temperature sensors or transducers to measure the compression or displacement. It is not limited to ultrasonic transducers and waveguides.

The accelerometer 902 can measure acceleration and static gravitational pull. It can include single-axis and multi-axis structures to detect magnitude and direction of the acceleration as a vector quantity, and can be used to sense orientation, vibration, impact and shock. The electronic circuitry 907 in conjunction with the accelerometer 902 and sensing assemblies 903 can measure parameters of interest (e.g., distributions of load, force, pressure, displacement, movement, rotation, torque and acceleration) relative to orientations of the sensing module with respect to a reference point. In such an arrangement, spatial distributions of the measured parameters relative to a chosen frame of reference can be computed and presented for real-time display.

The transceiver 920 comprises a transmitter 909 and an antenna 910 to permit wireless operation and telemetry functions. Once initiated the transceiver 920 can broadcast the parameters of interest in real-time. The telemetry data can be received and decoded with various receivers, or with a custom receiver. The wireless operation can eliminate distortion of, or limitations on, measurements caused by the potential for physical interference by, or limitations imposed by, wiring and cables connecting the sensing module with a power source or with associated data collection, storage, display equipment, and data processing equipment.

The transceiver 920 receives power from the energy storage 930 and can operate at low power over various radio frequencies by way of efficient power management schemes, for example, incorporated within the electronic circuitry 907. As one example, the transceiver 920 can transmit data at selected frequencies in a chosen mode of emission by way of the antenna 910. The selected frequencies can include, but are not limited to, ISM bands recognized in International Telecommunication Union regions 1, 2 and 3. A chosen mode of emission can be, but is not limited to, Gaussian Frequency Shift Keying, (GFSK), Amplitude Shift Keying (ASK), Phase Shift Keying (PSK), Minimum Shift Keying (MSK), Frequency Modulation (FM), Amplitude Modulation (AM), or other versions of frequency or amplitude modulation (e.g., binary, coherent, quadrature, etc.).

The antenna 910 can be integrated with components of the sensing module to provide the radio frequency transmission. The substrate for the antenna 910 and electrical connections with the electronic circuitry 907 can further include a matching network. This level of integration of the antenna and electronics enables reductions in the size and cost of wireless equipment. Potential applications may include, but are not limited to any type of short-range handheld, wearable, or other portable communication equipment where compact antennas are commonly used. This includes disposable modules or devices as well as reusable modules or devices and modules or devices for long-term use.

The energy storage 930 provides power to electronic components of the sensing module. It can be charged by wired energy transfer, short-distance wireless energy transfer or a combination thereof. External power sources can include, but are not limited to, a battery or batteries, an alternating current power supply, a radio frequency receiver, an electromagnetic induction coil, a photoelectric cell or cells, a thermocouple or thermocouples, or an ultrasound transducer or transducers. By way of the energy storage 930, the sensing module can be operated with a single charge until the internal energy is drained. It can be recharged periodically to enable continuous operation. The energy storage 930 can utilize common power management technologies such as replaceable batteries, supply regulation technologies, and charging system technologies for supplying energy to the components of the sensing module to facilitate wireless applications.

The energy storage 930 minimizes additional sources of energy radiation required to power the sensing module during measurement operations. In one embodiment, as illustrated, the energy storage 930 can include a capacitive energy storage device 908 and an induction coil 911. External source of charging power can be coupled wirelessly to the capacitive energy storage device 908 through the electromagnetic induction coil or coils 911 by way of inductive charging. The charging operation can be controlled by power management systems designed into, or with, the electronic circuitry 907. As one example, during operation of electronic circuitry 907, power can be transferred from capacitive energy storage device 908 by way of efficient step-up and step-down voltage conversion circuitry. This conserves operating power of circuit blocks at a minimum voltage level to support the required level of performance.

In one configuration, the energy storage 930 can further serve to communicate downlink data to the transceiver 920 during a recharging operation. For instance, downlink control data can be modulated onto the energy source signal and thereafter demodulated from the induction coil 911 by way of electronic control circuitry 907. This can serve as a more efficient way for receiving downlink data instead of configuring the transceiver 920 for both uplink and downlink operation. As one example, downlink data can include updated control parameters that the sensing module 900 uses when making a measurement, such as external positional information, or for recalibration purposes, such as spring biasing. It can also be used to download a serial number or other identification data.

The electronic circuitry 907 manages and controls various operations of the components of the sensing module, such as sensing, power management, telemetry, and acceleration sensing. It can include analog circuits, digital circuits, integrated circuits, discrete components, or any combination thereof. In one arrangement, it can be partitioned among integrated circuits and discrete components to minimize power consumption without compromising performance. Partitioning functions between digital and analog circuit enhances design flexibility and facilitates minimizing power consumption without sacrificing functionality or performance. Accordingly, the electronic circuitry 907 can comprise one or more Application Specific Integrated Circuit (ASIC) chips, for example, specific to a core signal processing algorithm.

In another arrangement, the electronic circuitry can comprise a controller such as a programmable processor, a Digital Signal Processor (DSP), a microcontroller, or a microprocessor, with associated storage memory and logic. The controller can utilize computing technologies with associated storage memory such a Flash, ROM, RAM, SRAM, DRAM or other like technologies for controlling operations of the aforementioned components of the sensing module. In one arrangement, the storage memory may store one or more sets of instructions (e.g., software) embodying any one or more of the methodologies or functions described herein. The instructions may also reside, completely or at least partially, within other memory, and/or a processor during execution thereof by another processor or computer system.

FIG. 10, depicts a cross sectional view of a sensing module 1000 in further detail according to one embodiment. As shown, sensing module 1000 includes components of the block diagram of FIG. 9. Sensing module 1000 is in a housing that can be made very low profile that includes a power source and telemetry to send data. Notably it can be shaped in a variety of ways such that it can placed or engaged or affixed to or within a component or components such that the medium, in this example, a waveguide 1010 is affected by or subjected to the parameter to be measured. In the non-limiting example, sensing module 1000 is subjected to an applied force on the upper and lower surfaces that compresses waveguide 1010. The amount of compression of waveguide 1010 can be measured using the pulse mode technique disclosed herein. The measured change in length of waveguide 1010 can be correlated to a pressure or force based on the material properties of waveguide 1010 (e.g. how much force it takes to deform the material per unit length change) and the conditions at the time of the measurement.

In this configuration, the sensing module 1000 can be hermetically sealed to measure parameters of interest within a wide range of applications including, but not limited to, applications within adverse environments, long-term applications, or medical applications. It can also be constructed in a wide range of sizes from very compact to large as required to fit the application. The hermetic sealing facilitates real time measurement and communication of physiological parameters within hostile environments.

The sensing module 1000 can be used in applications that require measurement of, but not limited to, load, force, pressure distance, weight, strain, wear, vibration, viscosity, and density, or movement of portions of physical systems, or load, force, pressure placed upon, or movement of, physical systems or bodies themselves, or load, force, pressure, or movement caused by external objects in the environment of the physical systems or bodies, or combinations of these parameters. The sensing module 1000 can be ported to applications where the following attributes are preferred: measurement of parameters of interest in real time, communication of measured values in real time, exemplary accuracy and precision of measurements, or a wide range of sizes of the sensing and communication module or device to fit requirements of applications or environments (e.g., harsh environments, adverse conditions, etc.) within which the measurement data is captured, or any combination of these attributes.

The components of sensing module 1000 comprise the waveguide 1010, the piezoelectric transducer 1012 and the reflective surface 1024. The piezoelectric device can be an ultrasonic transducer, resonator, or other type of transducer such as a micro-machined structure. A transducer is a generic term for a device that translates energy from one form to another while preserving key attribute e.g., same frequency, phase, duration, repetition rate. A transducer is a device that is actuated by power from one system and that supplies power usually in another form to a second system, for example, a loudspeaker.

The minimum thickness of sensing module 1000 comprises a stack of piezoelectric transducer 1012, waveguide 1010, and reflective surface 1024. In the embodiment, one or more transducer/waveguide stacks are used. The location where the pressure or force is applied on top cover 1002 can be determined by operatively locating three stacks around a contact area. Differences in pressure measurements from the three stacks can determine the location. For example, pressure applied in the center between the stacks will result in equal pressure readings (e.g., the contact area is centered). Conversely, different pressure readings between the three stacks will move the contact area closer towards the higher reading and farther from the stack with the lowest reading. An upper portion of sensing module 1000 comprises stacks, flexible interconnect, spring retainers 1006, and spring posts 1014. The upper portion of sensing module 1000 resides between top steel plate 1004 and printed circuit board 1018. A cup 1020 is the support structure for sensing module 1000. Cup 1020 supports printed circuit board 1018. Cup 1020 includes cavities for housing circuitry on a lower surface of printed circuit board 1018. A top cover couples to cup 1020 covering top steel plate 1004.

As previously indicated, accurate measurements of the amplitude and position of the load are achieved by measuring propagation time of ultrasonic waves or pulses within the flexible waveguide 1010 (or waveguides as other embodiments will include multiple springs and waveguides). The relationship of the propagation of ultrasound in a medium with respect to the aspect ratio of the piezoelectric element is well known. Ultrasound waves propagate linearly through the waveguide thus maintaining an accurate relationship between compression or extension and transit time of ultrasound waves. This enables accurate conversion of mechanical changes in the length or compression or extension of the waveguide into changes in the transit time of ultrasound waves or pulses within the waveguide. Moreover, piezoelectric transducer 1012, waveguide 1010, and reflective surface 1024 in conjunction with the mechanical supports (e.g., biasing springs) are uniquely calibrated by design to produce specific measurable and deterministic physical response to load or displacement.

FIG. 11 is a communication network 1100 for sensing applications in accordance with an exemplary embodiment. Briefly, the communication network 1100 expands the sensing system 1155 of FIG. 9 to provide broad data connectivity to other devices or services. As illustrated, the sensing system 1155 can be communicatively coupled to the communications network 1100 and any associated systems or services.

As one example, the sensing system 1155 can share its parameters of interest (e.g., distributions of load, force, pressure, displacement, vibration, viscosity, movement, rotation, torque and acceleration) with remote services or providers, for instance, to analyze or report on a status or outcome. The communication network 1100 can further be tied to a records system to implement rigorous information technology practices. In general, the sensing system can be linked to different information technology systems and software applications to communicate, to exchange data accurately, effectively, and consistently, and to use the exchanged data.

The communications network 1100 can provide wired or wireless connectivity over a Local Area Network (LAN) 1101, a Wireless Local Area Network (WLAN) 1105, a Cellular Network 1114, and/or other radio frequency (RF) system. The LAN 1101 and WLAN 1105 can be communicatively coupled to the Internet 1120, for example, through a central office. The central office can house common network switching equipment for distributing telecommunication services. Telecommunication services can include traditional POTS (Plain Old Telephone Service) and broadband services such as cable, HDTV, DSL, VoIP (Voice over Internet Protocol), IPTV (Internet Protocol Television), Internet services, and so on.

The communication network 1100 can utilize common computing and communications technologies to support circuit-switched and/or packet-switched communications. Each of the standards for Internet 1120 and other packet switched network transmission (e.g., TCP/IP, UDP/IP, HTML, HTTP, RTP, MMS, SMS) represent examples of the state of the art. Such standards are periodically superseded by faster or more efficient equivalents having essentially the same functions. Accordingly, replacement standards and protocols having the same functions are considered equivalent.

The cellular network 1114 can support voice and data services over a number of access technologies such as GSM-GPRS, EDGE, CDMA, UMTS, WiMAX, 2G, 3G, WAP, software defined radio (SDR), and other known technologies. The cellular network 1114 can be coupled to base receiver 1110 under a frequency-reuse plan for communicating with mobile devices 1102.

The base receiver 1110, in turn, can connect the mobile device 1102 to the Internet 1120 over a packet switched link. The internet 1120 can support application services and service layers for distributing data from the sensing system 1155 to the mobile device 1102. The mobile device 1102 can also connect to other communication devices through the Internet 1120 using a wireless communication channel.

The mobile device 1102 can also connect to the Internet 1120 over the WLAN 1105. Wireless Local Access Networks (WLANs) provide wireless access within a local geographical area. WLANs are typically composed of a cluster of Access Points (APs) 1104 also known as base stations. The sensing system 1155 can communicate with other WLAN stations such as laptop 1103 within the base station area. In typical WLAN implementations, the physical layer uses a variety of technologies such as 802.11b or 802.11g WLAN technologies. The physical layer may use infrared, frequency hopping spread spectrum in the 2.4 GHz Band, direct sequence spread spectrum in the 2.4 GHz Band, or other access technologies, for example, in the 5.8 GHz ISM band or higher ISM bands (e.g., 24 GHz, etc).

By way of the communication network 1100, the sensing system 1155 can establish connections with a remote server 1130 on the network and with other mobile devices for exchanging data. The remote server 1130 can have access to a database 1140 that is stored locally or remotely and can contain application specific data. The remote server 1130 can also host application services directly, or over the internet 1120.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

What is claimed is:

1. A low power measurement system for measuring a parameter comprising:
   a medium where the parameter to be measured affects the medium;
   a transducer coupled to the medium at a first location where the transducer emits a pulsed energy wave into the medium in response to a pulse; and
   a reflective surface coupled to the medium at a second location where the pulsed energy wave propagates through the medium to the second location and where the reflective surface reflects the pulsed energy wave back to the first location; and
   a pulsed system including:
      an edge detect circuit for detecting an edge of a signal from the transducer; and
      a first pulse circuit far generating a pulse to initiate a subsequent measurement sequence in response to a detected edge by the edge detect circuit where a transit time of the pulsed energy wave is measured and the transit time or change in transit time corresponds to the parameter where the system includes an amplifier having an input coupled to an output of the edge detect circuit and an output coupled to the transducer.

2. The system of claim 1 where the medium is a waveguide for containing and directing the pulsed energy wave.

3. The system of claim 2 where the waveguide comprises polyethylene and where the waveguide is cylindrical.

4. The system of claim 1 where the amplifier includes circuitry to dampen a wave shape for optimal transmission and reception in accordance with a matched network.

5. The system of claim 4 further including a second pulse circuit for providing one or more pulses to the transducer to initiate a sensing process, where the second pulse circuit is decoupled from the transducer when the edge detect circuit detects an edge of a first pulsed energy wave.

6. The system of claim 5 where the first pulse circuit is coupled to the input of the transducer to provide the-pulse to initiate the next measurement sequence-when the second pulse circuit is decoupled from the first transducer.

7. The system of claim 6 where the pulsed system modulates a time period of pulsed energy waves as a function of changes in distance or velocity through the medium.

8. The system of claim 1 where each pulsed energy wave is a damped ringing waveform where the edge detect circuit detects a leading edge of each pulsed energy wave and where upon detecting, the leading edge of each pulsed energy wave, the edge detect circuit is configured to be disabled from edge detecting for a predetermined period of time.

9. The system of claim 1 where the transit time is the sum of a pulsed energy wave propagating time from the first location to the second location of the medium and a pulsed energy wave propagating time from the second location to the first location of the medium.

10. The system of claim 9 further comprising a digital block for digitizing the frequency of operation of the pulsed system where the frequency corresponds to a time period of one or more pulsed energy waves.

11. The system of claim 1 where a force applied to the medium produces a proportional change in length of the medium.

12. The system at claim 1 where the medium comprises bone.

13. A method of measuring a parameter comprising the steps of:
- maintaining at least one pulsed energy wave in a medium subjected to the parameter being measured comprising the steps of:
  - detecting a first pulsed energy wave of the at least one pulsed energy waves reflected back to a first location with an edge detect circuit;
  - preventing a first pulse circuit from providing further pulses;
  - generating a pulse from a second pulse circuit upon detecting the first pulsed energy wave; and
  - emitting a pulsed energy wave into the medium at first location in response to each detected pulsed energy wave reflected back to the first location;
- initiating measurement by providing a fixed integer number of pulsed energy waves to the medium from the second pulse circuit;
- measuring a transit time of each pulsed energy wave with a timer where the transit time comprises each pulsed energy wave traversing the medium to the second location, being reflected by a reflector at a second location and traversing the medium to the first location; and
- relating the transit time to the parameter being measured.

14. The method of claim 13 further including the steps of:
- forming the medium of polymer having a predetermined height and cross-sectional area;
- coupling a piezoelectric transducer to the first location of the medium; and
- coupling a reflecting surface to the medium at a second location where a pressure or force is applied to either the first location, the second location, or both to produce a change in length of the medium thereby producing a corresponding transit time or time period of a pulsed energy wave therethrough.

* * * * *

UNITED STATES PATENT AND TRADEMARK OFFICE
CERTIFICATE OF CORRECTION

PATENT NO. : 8,421,479 B2
APPLICATION NO. : 12/748088
DATED : April 16, 2013
INVENTOR(S) : Stein It is certified that error appears in the above-identified patent and that said Letters Patent is hereby corrected as shown below:

Title page, Item (73) Assignee: Delete "NaviSense, Plantation FL (US)" and replace with --Orthosensor Inc. Sunrise, FL (US)--.

Signed and Sealed this
Fourteenth Day of May, 2013

Teresa Stanek Rea
*Acting Director of the United States Patent and Trademark Office*

UNITED STATES PATENT AND TRADEMARK OFFICE
CERTIFICATE OF CORRECTION

PATENT NO. : 8,421,479 B2
APPLICATION NO. : 12/748088
DATED : April 16, 2013
INVENTOR(S) : Marc Stein Page 1 of 1

It is certified that error appears in the above-identified patent and that said Letters Patent is hereby corrected as shown below:

On the title page item 73, should be corrected to read as

Assignee: Orthosensor Inc. Dania Beach FL 33004

Signed and Sealed this
Third Day of May, 2016

Michelle K. Lee
*Director of the United States Patent and Trademark Office*